United States Patent [19]

Budavari

[11] 4,440,942
[45] Apr. 3, 1984

[54] CRYSTALLINE DIASTEREOMERIC L-ALPHA-METHYLDOPA POE ESTER AND PROCESS FOR ITS PREPARATION

[75] Inventor: John Budavari, Watchung, N.J.

[73] Assignee: Merck & Co., Inc., Rahway, N.J.

[21] Appl. No.: 353,697

[22] Filed: Mar. 1, 1982

[51] Int. Cl.$^3$ .................................. C07C 101/08
[52] U.S. Cl. ......................................... 560/40
[58] Field of Search ............................. 560/40

[56] References Cited

U.S. PATENT DOCUMENTS 3,983,138  9/1976  Saari .
3,988,341  10/1976  Saari et al. .

OTHER PUBLICATIONS

Saari et al. (II), J. Med. Chem., vol. 21 (1978) 746–753.

*Primary Examiner*—Bernard Helfin
*Attorney, Agent, or Firm*—Alice O. Robertson; Ernest V. Linek

[57] ABSTRACT

Disclosed is a crystalline form of diastereomeric L-α-methyldopa POE ester, also referred to as, (R), (S)-α-pivaloyloxyethyl-(S)-3-(3,4-dihydroxyphenyl)-2-methylalaninate and a process for its isolation. Also disclosed is an improved process for the formation of diastereomeric L-α-methyldopa POE ester.

16 Claims, No Drawings

CRYSTALLINE DIASTEREOMERIC L-ALPHA-METHYLDOPA POE ESTER AND PROCESS FOR ITS PREPARATION

BACKGROUND OF THE INVENTION

This invention is directed to crystalline (R),(S)-α-pivaloyloxyethyl-(S)-3-(3,4-dihydroxyphenyl)-2-methylalaninate also referred to herein as "diastereomeric L-α-methyldopa POE ester" (wherein α-pivaloyloxyethyl is abreviated POE and (S)-3-(3,4-dihydroxyphenyl)-2-methylalanine is referred to by its more common name L-α-methyldopa), and a process for its isolation from a crude reaction mixture.

The diastereomeric mixture of (R)- and (S)-isomers of L-α-methyldopa POE ester is a known antihypertensive compound of Formula (I), see Saari et al., U.S. Pat. No. 3,983,138, which is herein incorporated by reference.

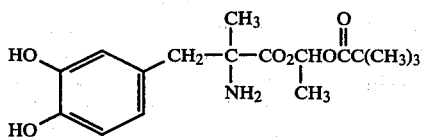

SUMMARY OF THE INVENTION

Crystalline diastereomeric L-α-methyldopa POE ester is isolated from the crude reaction mixture comprised of the desired compound, unreacted starting materials, reaction by-products and the reaction solvent by extraction.

There is also disclosed herein an improved process for the formation of diastereomeric L-α-methyldopa POE ester.

The diastereomeric free base mixture isolated as an intermediate in the process described by Saari et al., *Journal of Medicinal Chemistry* 21 746, 752 (1978) (See Example 4t) is described as a gummy residue, which would be unacceptable in pharmaceutical formulations. By virtue of the isolation process of the instant invention, a crystalline form of the diastereomeric mixture of L-α-methyldopa POE ester is now available for pharmaceutical compounding and/or for conversion to pharmaceutically acceptable salts.

DETAILED DESCRIPTION OF THE INVENTION

Crystalline, diastereomeric L-α-methyldopa POE ester is isolated from the reaction mixture of L-α-methyldopa and α-chloroethylpivalate and a dipolar aprotic solvent selected from: tetramethylurea, 1,3-dimethyl-2-imidazolidinone, N,N-diethyl and N,N-dimethyl acetamide, dimethylformamide, N-ethylpyrollidinone, N-formylpiperidine, and others as described in Saari et al., U.S. Pat. No. 3,988,341 which is herein incorporated by reference.

It has also been discovered that the addition of molecular sieves to the reaction medium of the Saari et al. patented process aids in the reduction of by-product formation and results in substantially higher yields. The molecular sieves may be in any convenient form; powdered, pellets, or beads. Generally, the amount of sieves added to the reaction mixture is not critical, but a preferred amount is generally about 35 grams of molecular sieves for every 100 grams of L-α-methyldopa. The typical use sieves are the crystalline metal aluminosilicates commonly referred to by the descriptive pore size (in angstroms) designations of 3 A, 4 A, 5 A and 13X. These sieves are available from the Aldrich Chemical Company.

The preferred aprotic reaction solvent is tetramethylurea (TMU) in a solvent ratio of about 2 ml of TMU per gram of L-α-methyldopa. The esterification may be conducted at temperatures from −20° C. to about 150° C. with about 75° C. being the preferred reaction temperature when employing TMU.

Generally, the reaction time requies about 24 to 48 hours for optimum esterification. Isolation of the crystalline diastereomeric L-α-methyldopa POE ester is accomplished by a series of extractions which efficiently remove unreacted starting materials, reaction by-products, and the aprotic solvent. The extractions are generally conducted using a volume of extracting solvent equal to the volume being extracted. The extraction volume may vary from about 0.5 volumes to about 5 volumes.

The crude reaction mixture containing the desired ester, by-products and unreacted starting materials is brought to room temperature and diluted up to about four times by volume with an inert organic solvent. Typical useful solvents include the aromatic hydrocarbon solvents such as benzene, toluene, xylenes; halogenated aromatic hydrocarbons such as chlorobenzene and the like; $C_4$ to $C_8$ lower alkyl esters including ethyl acetate, n-propylacetate, isopropyl acetate, n-butyl acetate; tert-butyl acetate and the like; $C_4$ to $C_8$ lower alkyl ketones including methyl ethyl ketone and methyl isobutyl ketone; halogenated $C_1$ to $C_4$ lower alkyl compounds such as tert-butyl chloride, iso-butyl chloride, carbon tetra-chloride, chloroform, and methylene chloride; diethyl ether and the like. A preferred solvent is toluene. The diluted solution is thoroughly extracted with saturated aqueous sodium bicarbonate or a similar aqueous inorganic salt solution of comparable ionic solution strength. Generally, solutions having a minimum ionic solution strength of 5% (by weight), and up to a maximum ionic solution strength of saturation are suitable in this process. Generally the inorganic salts useful in the aqueous extractions are the mineral acid salts. For example, the chlorides, sulfates, carbonates, phosphates and nitrates of sodium, potassium, magnesium and calcium are useful in this process. Examples of suitable inorganic salts include: NaCl, $CaCl_2$, $NH_4Cl$, $Na_2SO_4$, KCl, $NaHCO_3$, $KHCO_3$, $MgSO_4$ and the like. The organic phase may be further washed with saturated sodium chloride solution, (especially if a bicarbonate wash has been employed) dried over a suitable drying agent such as sodium or magnesium sulfate and filtered.

The organic phase is then diluted with an apolar solvent. This dilution may vary from about 0.5 volumes to about 5 volumes. A preferred dilution is up to about 1 volume. Suitable apolar solvents include; cyclohexane, cycloheptane, cylooctane, acyclic $C_5$ to $C_8$ hydrocarbon solvents such as n-pentane, iso-pentane, neopentane, hexanes, heptanes, octanes; petroleum ether, diethyl ether, ligroin, Skellysolves A, B, C, D, E, F, G, H, and L (see *The Merck Index*, 9th ed. 1976, No. 8297). "Skellysolve" is a tradename of the Skelly Oil Co., Kansas City, Mo. A preferred apolar solvent is n-hexane. The diluted organic phase is then seeded with crystaline diastereomeric L-α-methyldopa POE ester (see preparation below), and aged at about 25° C. over a period of 1 hour and then at about 0° C. to 5° C. for about 16 hours. Generally the seed crystals are added to the diluted solution from about 0.5% by weight to 20% by weight of the available product in the solution as determined by HPLC analysis. Preferably the seeding is accomplished using from 1% by weight to 10% by weight of the available product. The crystalline product is collected by filtration and washed first with a mixture of hexane-toluene (1:1) then hexane only and dried in vacuo at ambient temperature.

The seed crystals employed in the above crystallization are prepared by the following procedure:

The crude reaction mixture containing the desired ester, by-products and unreacted starting materials is diluted with an inert solvent such as toluene. The solution is extracted with aqueous sodium bicarbonate to remove the aprotic solvent and reaction by-products. Further extractions with an aqueous mineral acid such as 2.5 N HCl and water (1X each) are made. Other useful aqueous acids to be included within the definition of "mineral acids" include $H_2SO_4$, $H_3PO_4$, $HNO_3$, acetic acid, trifluoroacetic acid and the like. The preferred acid concentration is about 2.5 N. These aqueous extracts are combined and mixed with $CH_2Cl_2$. Solid $NaHCO_3$ is added until the aqueous phase is basic. Other useful solid bases include sodium or potassium carbonate, sodium or potassium hydroxide, and potassium bicarbonate. The organic phase is concentrated to about ½ volume, and diluted with hexane. The vessel walls are scratched to induce crystal growth. The solution ages at 0° C. for up to seven days and the crystals are collected by filtration.

The following examples are provided to make more clear the process of the instant invention. All temperatures, unless otherwise specified, are in °C.

EXAMPLE I (R),(S)-α-pivaloyloxyethyl-(S)-3-(3,4-dihydroxyphenyl)-2-methylalaninate (seed crystal formation)

A mixture of 211.2 g (1.00 mole) L-α-methyldopa and 172 ml (165 g, 1.00 mole) of α-chloroethylpivalate in 422 ml of tetramethylurea (TMU) was warmed to 75° C. and stirred at 75°±2° for 27 hours. During the reaction time, complete dissolution was achieved. (NOTE: complete dissolution correspond to the maximum product conversion point).

The reaction mixture was cooled to room temperature (about 25° C.) and diluted with 1.6 liter of toluene. The diluted solution was extracted with 4×1 liter of saturated aqueous sodium bicarbonate solution. The initial bicarbonate wash had a pH of about 7.5.

The product-containing organic layer was next extracted with a mixture of 75 ml (0.87 mole) of concentrated hydrochloric acid diluted with 425 ml water and was then extracted with 100 ml of water. The aqueous portion of the acid extraction is combined with the aqueous layer from the water extract and admixed with 1 liter of methylene chloride. Solid sodium bicarbonate was added to the stirred mixture (CAUTION—foaming) to make the aqueous layer basic; approximately 90 g was required.

The methylene chloride layer was washed with 200 ml of water, 200 ml of brine (aqueous saturated NaCl), dried over about 50 g of magnesium sulfate and concentrated to a volume of about 700 ml. About 700 ml of hexane were added and the walls of the vessel were scratched to produce nucleation sites for crystal growth.

Over a period of about 2–3 hours another 1.15 liters of hexane were added and the slurry was aged at 0° to 5° C.

The crystalline product, (R),(S)-α-pivaloyloxyethyl-(S)-3-(3,4-dihydroxyphenyl)-2-methylalaninate, was collected by filtration, washed with 2×500 ml of hexane-methylene chloride (3:1) followed by 500 ml of hexane and dried in vacuo to yield 130 g (38.3%) m.p. 166°–119° C.

EXAMPLE II (R),(S)-α-pivaloyloxyethyl-(S)-3-(3,4-dihydroxyphenyl)-2-methylalaninate A mixture of 200 g (0.94 mole) of L-α-methyldopa, 190 ml (183 g, 1.10 mole) of α-chloroethylpivalate (98% pure by GLC analysis, 400 ml of tetramethylurea and 67 g of 4 A molecular sieves in a 3 l. round bottom flask fitted with a stirrer, $N_2$ inlet and immersion thermometer was warmed to 75° and stirred at 75° for 24 hours. During this time the L-α-methyldopa dissolved. The reaction mixture was diluted with 900 ml of toluene and filtered through a filter aid, Supercel (acid washed). The filtrate was then washed four times with 2 l of saturated aqueous sodium bicarbonate solution and once with 2 l of saturated aqueous sodium chloride at 15°–20°. The toluene layer was dried over 150 g of anhydrous sodium sulfate and filtered. The solid $Na_2SO_4$ was washed with 2×250 ml of toluene.

The filtrate and toluene washes were combined and diluted with 650 ml of hexane at 25° and seeded with about 10 g of the Example I seed crystals. Crystallization occured immediately. The mixture was aged for one hour at 25° cooled to 0° to 5° and aged for 16 hours at that temperature. The crude product was filtered, washed with 500 ml of toluene:hexane (1:1) and 500 ml of hexane. Drying at 25° in vacuo gave 240 g (75% yield) of crude diastereomeric-α-methyldopa POE ester, m.p. 117°–119° C.

EXAMPLE III

Recrystallization of diastereomeric-α-Methyldopa POE Ester

Crude diastereomeric-α-methyldopa POE Ester (50 g) from Example II was slurried for one hour in 650 ml of ethyl acetate at 25°. The insolubles were removed by filtration and washed with 2×100 ml of ethyl acetate. The filtrate was concentrated at 25° to 30° in vacuo to a volume of 550 ml. Approximately 550 ml of hexane were added at 25° and the solution was seeded with about 0.5 g of Example I seed crystals. Another 550 ml of hexane were added dropwise over 2½ hours during which time crystallization occurred. The mixture was cooled to 0° to 5° and aged at 0° to 5° for 16 hours. The product was filtered, washed with 2×100 ml of cold ethyl acetate:hexane (1:2) and 2×100 ml of hexane, and dried at 25° in vacuo to give 45 g (90% recovery) of crystalline diastereomeric-α-methyldopa POE ester, m.p. 120°–123° C.

What is claimed is:

1. Crystalline, diastereomeric L-α-methyldopa POE ester, also referred to as (R),(S)-α-pivaloyloxyethyl-(S)-3-(3,4-dihydroxyphenyl)-2-methylalaninate.

2. A process for isolating in a crystalline form, diastereomeric L-α-methyldopa POE ester from its crude reaction mixture which comprises:

(A) bringing said crude reaction mixture comprising diastereomeric L-α-methyldopa POE ester and an aprotic solvent to room temperature and diluting by up to about four times by volume with an inert organic solvent, (B) extracting the organic solvent solution with an aqueous inorganic salt solution of ionic solution strength of from 5% (by weight) to saturated, (C) finally, adding from about 0.5 to 5 volumes of an apolar solvent, aging the slurry, and collecting the resulting crystalline product.

3. The process of claim 2 which further comprises drying the organic phase from step (B) over a suitable drying agent, and concentrating the organic phase in vacuo.

4. The process of claims 2 or 3 which further comprises the adding of seed crystals of diastereomeric L-α-methyldopa POE ester to the step (C) mixture prior to aging the slurry.

5. A process for isolating in a crystalline form, diastereomeric L-α-methyldopa POE ester from its crude reaction mixture which comprises:

(A) bringing said crude reaction mixture comprising diastereomeric L-α-methyldopa POE ester and an inert aprotic solvent to room temperature and diluting by up to about four times by volume with an inert organic solvent, (B) extracting the organic solvent solution with a from 5% (by weight) to saturated, aqueous inorganic salt solution, (C) extracting the organic solvent solution with an aqueous mineral acid solution, then (D) extracting the organic solvent solution with water, (E) combining the aqueous layers of steps (C) and (D), (F) admixing the combined aqueous extracts from step (E) with an organic solvent selected from methylene chloride, ethyl acetate, isopropyl acetate and toluene, (G) basifying the aqueous phase of the mixture in step (F) with a solid base selected from sodium bicarbonate, sodium carbonate, sodium hydroxide, potassium bicarbonate, potassium carbonate and potassium hydroxide, (H) washing the organic phase from step (G) with water, saturated NaCl and drying over a suitable drying agent, (I) finally, concentrating the organic phase, adding an apolar solvent, aging the slurry, and collecting the crystalline product.

6. The process of claims 2 or 5 wherein the aqueous inorganic salt solution concentration is from 5% to 50% by weight.

7. The process of claims 2 or 5 wherein the inert organic solvent is toluene, and the apolar solvent is hexane.

8. The process of claims 2 or 5 wherein the aprotic solvent is tetramethylurea.

9. The process of claims 2 or 5 wherein the aprotic solvent is 1,3-dimethyl-2-imidazolidinone.

10. The process of claims 2 or 5 wherein the aqueous inorganic salt solution of Step (B) is saturated aqueous sodium bicarbonate.

11. The process of claim 5 wherein the aqueous mineral acid of Step (C) is 2.5 N hydrochloric acid.

12. The process of claim 5 wherein the organic solvent of Step (F) is methylene chloride.

13. The process of claim 5 wherein the solid base of Step (G) is sodium bicarbonate.

14. In the process for preparing (R),(S)-α-pivaloyloxyethyl-(S)-(3,4-dihydroxyphenyl)-2-methylalaninate which comprises reaction L-α-methyldopa and α-chloroethylpivalate in an aprotic solvent; the improvement which comprises:

adding molecular sieves selected from the powder, pellet or bead form of sieve types 3 A, 4 A, 5 A or 13X, to the reaction mixture.

15. A process for isolating in a crystalline form, diastereomeric L-α-methyldopa POE ester from the crude reaction mixture of claim 14 which comprises:

(A) bringing said crude reaction mixture comprising diastereomeric L-α-methyldopa POE ester and an aprotic solvent to room temperature and diluting by up to about four times by volume with an inert organic solvent.

(B) filtering the diluted reaction mixture through a filter aid and, (C) extracting the organic solvent solution with an aqueous inorganic salt solution of ionic solution strength of from 5% (by weight) to saturated.

(D) finally, adding from about 0.5 to 5 volumes of an apolar solvent, aging the slurry, and collecting the resulting crystalline product.

16. The crystalline mixture, diastereomeric L-α-methyldopa POE ester, isolated from a crude reaction mixture comprising diastereomeric L-α-methyldopa POE ester, an aprotic solvent, unreacted starting materials and reaction by-products by the steps comprising:

(A) bringing said crude reaction mixture to room temperature and diluting by up to about four times by volume with an inert organic solvent, (B) extracting the organic solvent solution with an aqueous inorganic salt solution of ionic solution strength of from 5% (by weight) to saturated, (C) drying the organic solvent of Step (B) over a suitable drying agent, (D) finally, concentrating the organic phase, adding from about 0.5 to 5 volumes of an apolar solvent, adding seed crystals, aging the slurry.

* * * * *